United States Patent
Bosco et al.

(10) Patent No.: US 11,071,750 B2
(45) Date of Patent: Jul. 27, 2021

(54) SOLUBLE ADDUCTS OF BORIC ACID OR DERIVATIVES AND PRECURSORS THEREOF WITH CHITOSAN OLIGOSACCHARIDE DERIVATIVES

(71) Applicants: BIOPOLIFE SRL, Trieste (IT); UNIVERSITA' DEGLI STUDI DI TRIESTE, Trieste (IT)

(72) Inventors: Marco Bosco, Gradisca D'isonzo (IT); Massimiliano Borgogna, Trieste (IT); Andrea Travan, Trieste (IT); Ivan Donati, Sedegliano (IT)

(73) Assignees: BIOPOLIFE SRL, Trieste (IT), part interest; UNIVERSITA' DEGLI STUDI DI TRIESTE, Trieste (IT), part interest ( * ) Notice: Subject to any disclaimer, the term of this patent is extended or adjusted under 35 U.S.C. 154(b) by 18 days.

(21) Appl. No.: 16/471,042

(22) PCT Filed: Dec. 21, 2017

(86) PCT No.: PCT/IB2017/058247
§ 371 (c)(1),
(2) Date: Jun. 19, 2019

(87) PCT Pub. No.: WO2018/116224
PCT Pub. Date: Jun. 28, 2018

(65) Prior Publication Data
US 2020/0113929 A1    Apr. 16, 2020

(30) Foreign Application Priority Data
Dec. 22, 2016   (IT) .................. 102016000130342

(51) Int. Cl.
*A61K 31/722* (2006.01)
*A61K 8/73* (2006.01)
*A61K 33/22* (2006.01)

(52) U.S. Cl.
CPC ............ *A61K 31/722* (2013.01); *A61K 8/736* (2013.01); *A61K 33/22* (2013.01)

(58) Field of Classification Search
None
See application file for complete search history.

(56) References Cited

U.S. PATENT DOCUMENTS

| | | |
|---|---|---|
| 4,424,346 A | 1/1984 | Hall et al. |
| 5,747,475 A | 5/1998 | Nordquist et al. |
| 6,277,792 B1 | 8/2001 | House |

FOREIGN PATENT DOCUMENTS

| | | |
|---|---|---|
| EP | 2029629 A1 | 3/2009 |
| EP | 2310448 A1 | 4/2011 |
| WO | 2007135116 A1 | 11/2007 |
| WO | 2010010122 A1 | 1/2010 |
| WO | 2015073075 A1 | 5/2015 |

OTHER PUBLICATIONS

Donati, Biomaterials 26 (2005) 987-988. (Year: 2005).*
Avinash, Int. J. PharmTech Res. 2014-2015, 7(4), pp. 668-674. (Year: 2014).*
Search Report and Written Opinion of PCT/IB2017/058247 dated Mar. 6, 2018.

* cited by examiner

*Primary Examiner* — Layla D Berry
(74) *Attorney, Agent, or Firm* — Silvia Salvadori, P.C.; Silvia Salvadori

(57) ABSTRACT

Disclosed are adducts of boric acid and chitosan wherein the amino groups of the D-glucosamine units are bonded to residues of polyol or alditol oligosaccharides, the molar ratio between boric acid and the repeating chitosan unit ranging between 0.001 and 4.

9 Claims, 2 Drawing Sheets

SOLUBLE ADDUCTS OF BORIC ACID OR DERIVATIVES AND PRECURSORS THEREOF WITH CHITOSAN OLIGOSACCHARIDE DERIVATIVES

This application is a U.S. national stage of PCT/IB2017/058247 filed on 21 Dec. 2017, which claims priority to and the benefit of Italian Application No. 102016000130342 filed on 22 Dec. 2016, the contents of which are incorporated herein by reference in their entireties.

The present invention relates to soluble polymeric adducts between boric acid or derivatives and precursors thereof and chitosan oligosaccharide derivatives, which do not form hydrogels at concentrations ranging between 3% and 5%, and their synthesis and use in the cosmetic, biomedical and pharmaceutical fields, especially for applications as a viscosupplement, elasticiser and adhesive.

Prior art Polysaccharides are known to be biopolymers of great application interest in view of their high biocompatibility and particular physicochemical properties, especially due to the complex rheological responses that make them suitable for multiple applications in the fields of viscosupplementation, ophthalmology, ophthalmic surgery and cosmetics.

Chitosan, a polysaccharide widely available in nature, is obtained by chemical deacetylation from chitin, the main constituent of the exoskeleton of crustaceans. Chitosan mainly consists of glucosamine units alternating with N-acetylglucosamine units. Said polysaccharide is insoluble in basic or neutral aqueous solutions unless the pH of the solution is adjusted to a value of 5 or less. For this reason, numerous chemical modifications of chitosan have been proposed over the years, especially regarding the amino functions of the polysaccharide, to overcome this limitation and modify its physicochemical properties.

U.S. Pat. No. 4,424,346 (Yalpani-Hall) describes the synthesis of chitosan derivatives obtained by inserting oligosaccharide residues on the amino function. The same patent states that aqueous solutions of said chitosan oligosaccharide derivatives, in particular those obtained with glucose, lactose and maltose, form rigid hydrogels at polymer concentrations ranging between 3% and 5%.

In EP 2021408, chitosan oligosaccharide derivatives were mixed with polyanions such as hyaluronic acid and alginate to increase their viscosity and viscoelastic response and prevent their coacervation.

In U.S. Pat. No. 6,277,792, chitosan was modified in a similar way to the method presented in U.S. Pat. No. 4,424,346, to increase the viscosity of its aqueous solutions. In U.S. Pat. No. 6,277,792 the synthesis method involves the use of a temperature exceeding 60° C. and a pH value of less than 4.5.

U.S. Pat. No. 5,747,475 describes branched chitosans with oligosaccharides and their application, mainly as immunostimulants in the field of photodynamic tumour therapy. Said document does not provide any structural characterisation of the derivatives; in particular, the degree of substitution of oligosaccharide conjugate (DS) is not measured, nor is the possible boron residue in the end product quantified. Moreover, the document fails to clarify whether or to what extent the possible presence of boron affects the properties of the polymer.

Boric acid is known to form esters with diols or polyols in aqueous solution (van Duin M. et al., Tetrahedron, 40, 1984, 2901-2911; Van Duin M. et al., Tetrahedron, 41, 1985, 3411-3421). Said esters are often exploited for analytical purposes in the analysis of polyhydroxy compounds such as carbohydrates (Hoffstetter-Kuhn S. et al., Anal. Chem., 63, 1991, 1541-1547; Landers J. P. et al., Anal. Chem., 64, 1992, 2846-2851).

It is also known that the complexes formed between boron and diol, in the case of polysaccharides like galactomannans, are highly sensitive to the pH value of the solution. In particular, Pezron et al. (Macromolecules; 1988; 21; 1121-1125) demonstrated that said complexes are not formed at pH values below about 7.5.

Boric acid and derivatives thereof are known for their ability to bond to diols, consequently acting as crosslinking agents of polysaccharides having glucose side chains (scleroglucan) or galactose side chains (guar gum) (Bocchinfuso G. et al, J. Phys. Chem. B, 2010, 114, 13059-13068).

U.S. Pat. No. 7,195,065 describes the use of boric acid and derivatives thereof as a crosslinking agent of guar gum or derivatives thereof to produce hydrogels for the treatment of subterranean formations.

EP 2310448 describes three-dimensional composite materials containing metal nanoparticles associated with polysaccharides that possess an antibacterial action and low cytotoxicity. Said metal particles are stabilised by chitosans conjugated with oligosaccharides.

EP 2029629 describes the preparation of three-dimensional hydrogels characterised by the mixture of acid polysaccharides (anionic) and chitosans conjugated with oligosaccharides (cationic) as matrices for encapsulation of cells or pharmaceutical ingredients.

WO 2010/010122 describes materials consisting of metal particles stabilised by chitosans conjugated with oligosaccharides having regular nanometric dimensions suitable for applications in the biomedical and bio sensor fields.

The chitosans conjugated with oligosaccharides described in said EP 2310448, EP 2029629, WO 2010/010122 and WO 2007/135116 are obtained by a process involving a low concentration of chitosan ($\approx$0.9% w/V) in a solvent consisting of a 50% (V/V) water and methanol mixture containing 1% w/V acetic acid, with an acetic acid/chitosan molar ratio=3.15 at a strongly acid pH (pH=4.5). The reaction is conducted at room temperature for 24 hours at a constant pH, at both the purification stage and the product isolation stage. The purification is conducted by dialysis.

Said documents do not provide any information about the presence of boron bonded to said polymers; although they are obtained with a boron-based reducing agent ($NaCNBH_3$), the residual amount of boron in the final polysaccharide is unknown, and the rheological behaviour of said polymers does not differ from that described for polysaccharides in general. The comparative tests reported below demonstrate that the derivatives obtained by known methods have a boron content well below 0.001 moles to the moles of polymer.

The increase in polymer concentration at the synthesis stage is known to have major industrial importance, as it allows higher mass yields, and purification processes that use smaller amounts of solvents. However, in many cases the higher concentration leads to poorly soluble products.

The formation of hydrogels makes these systems unsuitable for use as injectables in the biomedical field (joint or ophthalmic applications) or the cosmetic field (cosmetic fillers, moisturising creams), because if hydrogels are subjected to a mechanical force, they cannot deform indefinitely without breakage, and therefore do not perform an effective lubricating action, and cannot be spread evenly. Conversely, solutions with sufficiently high viscoelasticity possess excellent tenacity, a property crucial for applications in the fields of viscosupplementation and adhesives.

DESCRIPTION OF THE INVENTION

It has now been found that boric acid adducts with chitosan derivatives functionalised with oligosaccharides increase viscosity and viscoelastic response without the formation of hydrogels, even in concentrated solutions. Compact, soluble adducts can be obtained when a ratio ranging from 0.001 and 4 between the molarity of the boron derivatives and the molarity of the chitosan, in terms of repeating polymer units, is maintained in the structure obtained after the synthesis and purification process.

"Repeating polymer unit" here signifies the mean repeating unit of the chitosan oligosaccharide derivatives calculated on the basis of the polymer composition obtained from $^1$H-NMR analysis.

A first aspect of the invention therefore relates to adducts of boric acid and chitosan wherein the amino groups of the D-glucosamine units are bonded to polyol or alditol oligosaccharide residues, the molar ratio between boric acid and the repeating chitosan unit ranging between 0.001 and 4.

A second aspect of the invention relates to a process for the preparation of the adducts which comprises:
 a) adding boric acid, derivatives or precursors thereof and oligosaccharide to a chitosan aqueous solution at a polymer concentration greater than or equal to 1.5%;
 b) purifying the soluble adducts obtained at stage a) with the use of non-solvents and acid solutions.

The process according to the invention differs markedly from those described in EP 2310448, EP 2029629, WO 2010/010122 and WO 2007/135116 in the following respects:
 1. high chitosan concentration (3% w/V);
 2. the solvent consists only of water;
 3. the added acetic acid is measured in a stoichiometric amount (acetic acid/chitosan molar ratio=1) to the repeating chitosan units, i.e. in the amount strictly necessary to dissolve the polymer;
 4. the pH of the reaction medium is weakly acid, ranging between 5.5 and 6.0;
 5. the reaction is conducted at 60° C. for 4 hours;
 6. at the end of the reaction the crude product is acidified to pH=2.5, or alternatively, the polymer precipitated with alcohol is washed repeatedly with mixtures of alcohol and HCl;
 7. the crude reaction product is treated with alcohols or acetone until precipitation, and the solid is then washed with water/alcohol mixtures.

The oligosaccharides are selected from glucose, galactose, lactose, cellobiose, cellotriose, maltose, maltotriose, maltotetraose, chitobiose, chitotriose, melibiose, agarobiose and carrabiose. The preferred oligosaccharide is lactose.

Surprisingly, contrary to what is commonly expected, and what actually happens for the chitosan oligosaccharide derivatives of U.S. Pat. No. 4,424,346, the presence in the end product of encapsulated boric acid in the presence of a high concentration of polysaccharide does not lead to the formation of hydrogels at total polysaccharide concentrations ranging between 3% and 5% (w/V).

The adducts between boric acid and the chitosan derivatives according to the invention possess unusual rheological properties. In fact, the dependence of shear viscosity on polymer concentration follows a scaling law $\eta \propto C^\alpha$ wherein $\alpha$ preferably ranges between 4.5 and 6.2, and even more preferably is 5.8. Conversely, it is known from the literature that polysaccharides and the derivatives thereof typically have a coefficient $\alpha$ ranging between 3.1 and 3.3 (Morris E. R. et al., Carbohydr. Polym., 1981, 1, 5). This unusual rheological behaviour is of great interest for applications in the viscosupplementation field, because the modest increase in concentration of these soluble adducts gives rise to a great increase in viscosity; much greater than occurs in the absence of the soluble adducts.

DETAILED DESCRIPTION OF THE INVENTION

The adducts according to the invention are prepared by introducing boric acid or derivatives and precursors thereof during the synthesis and purification process of chitosan oligosaccharide derivatives. An essential feature of the process is that the boric acid or precursors and derivatives thereof are encapsulated in a phase having a high polysaccharide concentration, and the soluble adducts are purified with non-solvents and acid solutions. Examples of non-solvents include methanol, ethanol, isopropanol, n-propanol and acetone. Examples of acids include hydrochloric, nitric, acetic, formic, trichloroacetic, trifluoroacetic, sulphuric and phosphoric acids and combinations thereof.

To obtain soluble adducts, the chitosan derivatives must have a degree of substitution of the amino groups with the oligosaccharide side chain ranging between 30% and 80%, preferably 60%. The average molecular weight (hereinafter called MW) of chitosan usable for the production of soluble adducts can be up to 1500 kDa, and preferably ranges between 300 kDa and 1000 kDa.

The soluble adducts can be obtained by using boric acid or derivatives and precursors thereof such as sodium borohydride, sodium cyanoborohydride, sodium acetate borohydride, sodium triacetoxyborohydride, lithium borohydride, potassium borohydride, tetrabutylammonium borohydride, calcium borohydride, magnesium borohydride, tetraethylammonium borohydride, methyltrioctylammonium borohydride, bis(triphenylphosphine) copper (I) borohydride, borax, potassium tri(1-pyrazolyl) borohydride, cetyltrimethylammonium borohydride, tetrahydrofuran-borane complex, picoline-borane complex, dimethylsulphide-borane complex, pyridine-borane complex, trimethylamine-borane complex, triethylamine-borane complex, morpholine-borane complex, t-butylamine-borane complex, ammonia-borane complex, diphenylphosphine-borane complex, 4-methylmorpholine-borane complex and ethylenediamine-borane complex. The boric acid derivatives used are preferably sodium cyanoborohydride and picoline-borane complex, generally a borane complexed with a heterocyclic aromatic nitrogen compound, and more preferably picoline-borane complex.

The increase in polymer concentration at the synthesis stage and the inclusion therein of boric acid and derivatives or precursors thereof gives rise to adducts which remain soluble at polymer concentrations ranging between 3% and 5%.

In this way, the ratio between the moles of boric acid and the moles of repeating polymer units can be fine-tuned so that it is not less than 0.001 and not more than 4.

Unlike U.S. Pat. No. 4,424,346, the presence of boric acid or derivatives and precursors thereof encapsulated in the adducts in a concentrated solution situation prevents the formation of hydrogels at polymer concentrations ranging between 3% and 5% (w/V). In fact, the adducts according to the invention remain soluble up to concentrations of 10% (w/V) without forming hydrogels.

Figure 1:
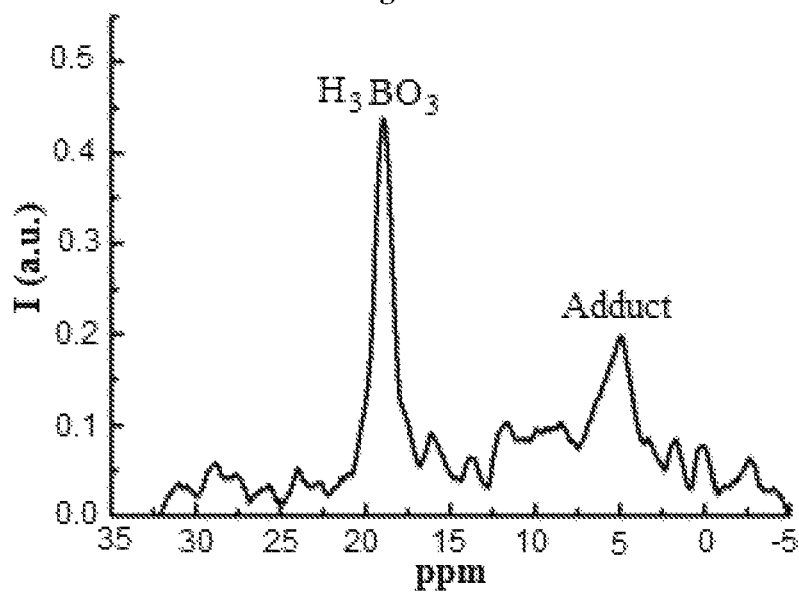
FIG. 1. $^{11}$B-NMR spectrum of an adduct between boric acid and a chitosan oligosaccharide derivative (CTL). The spectrum shows the signal of the adduct, which is very different from that of boric acid (added to the test solution for demonstration purposes only). Polymer concentration 0.9% (w/V), measurements conducted in PBS at pH 7.4.
Figure 2:
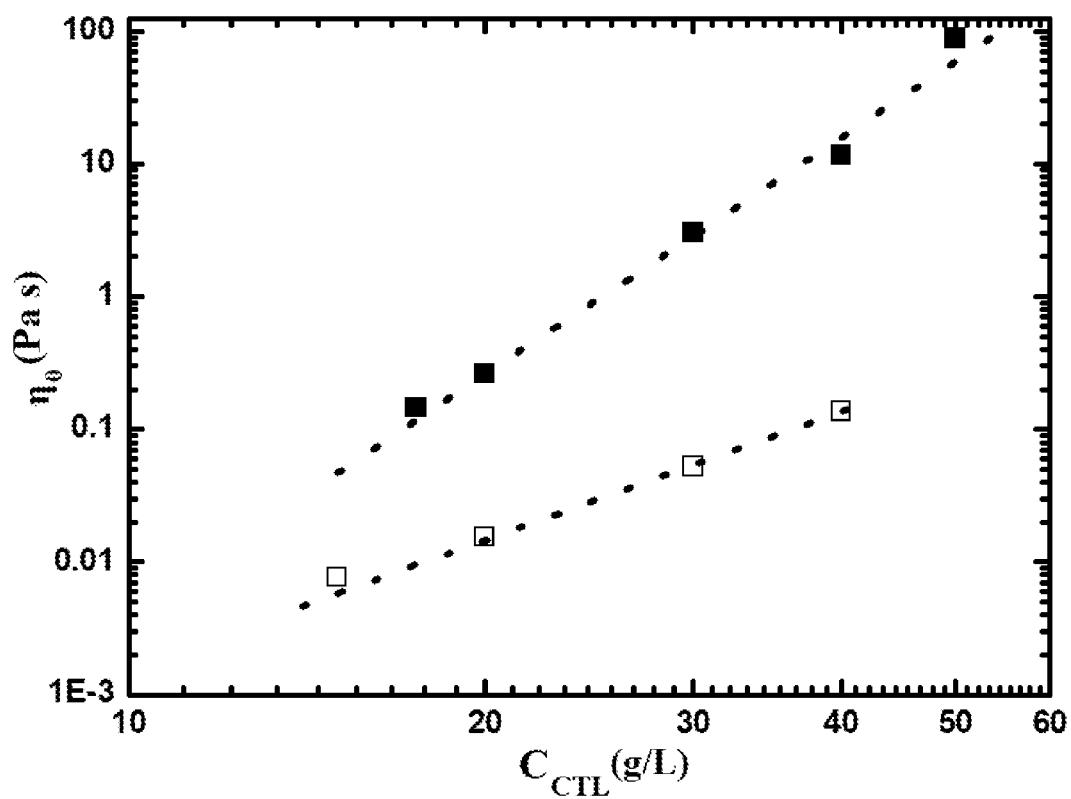
FIG. 2. Dependence of zero-shear-rate viscosity ($\eta_0$) on concentration of chitosan oligosaccharide derivatives ($C_{CTL}$) for soluble intramolecular aggregates at a [B]/[CTL]$_{ru}$ ratio of 0.018 (■) and for the chitosan oligosaccharide derivative prepared according to patents EP 2 310 448 A1, EP 2 029 629 A1, WO 2010/010122 A1 and WO 2007/135116 A1 (□). In this case the scaling law found is that expected for polysaccharides, namely $\eta_\square \propto C_{CTL}^{3.z}$.

The soluble adducts were analysed with the use of rheological measurements. Surprisingly, the flow curves recorded for solutions of the soluble adducts demonstrate that the dependence of the zero-shear-rate viscosity ($\eta_0$) presents a polymer concentration (C) scaling law of $\eta \propto C^{5.\square}$ with a $[B]/[C_{CTL}]$ ratio of 0.018 (FIG. 2). The latter proved to be considerably greater than that normally reported for polysaccharide solutions (Morris E. R. et al., Carbohydr. Polym., 1981, 1, 5), i.e. ranging between approximately $\eta \propto C^{3.\square}$ and $\eta \propto C^{3.a}$.

Figure 3:
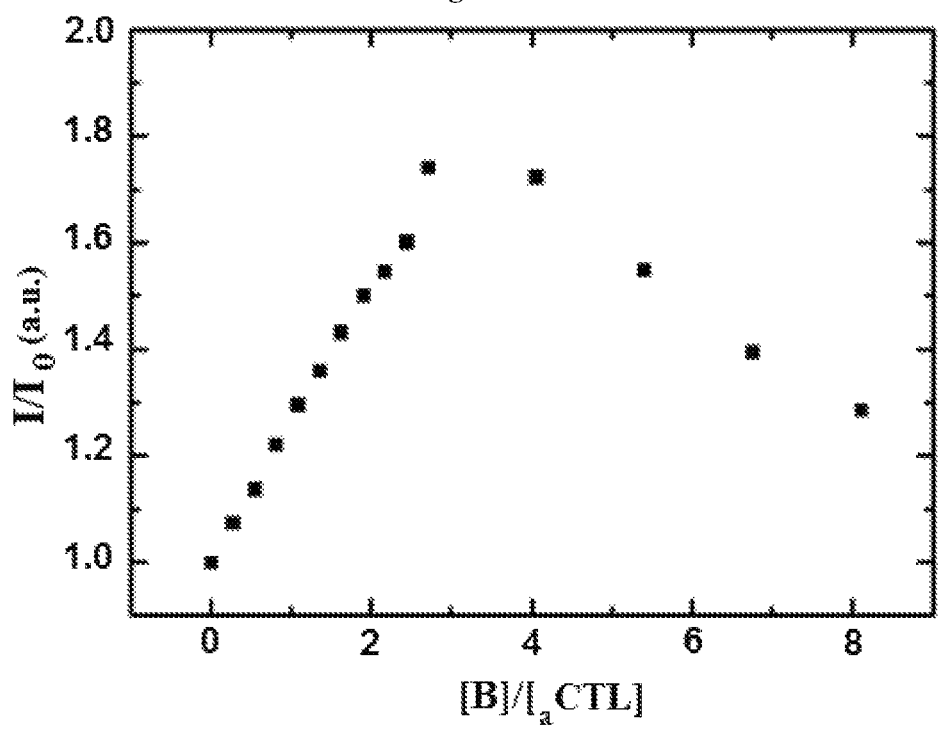
FIG. 3. Relative variation in diffused light of soluble aggregates with different amounts of boron ([B]/[C$_{CTL}$]) and a constant concentration of soluble adducts. Measurements conducted in PBS at pH 7.4.

FIG. 3 shows the relative variation in diffused light which increases, in the interval of interest for the present patent, proportionally to the boron in the soluble intramolecular aggregates, thus demonstrating that the molecular structure is more compacted.

The presence of soluble aggregates between boric acid or derivatives and precursors thereof and chitosan oligosaccharide derivatives gives rise to very pronounced, lasting formation of filaments, which is particularly interesting for all applications wherein the viscoelastic response is crucial, such as viscosupplementation, wound treatment, cosmetic and ophthalmic applications, and treatment of joint disorders. The adducts according to the invention can also be used in the field of biomaterials, sports medicine, as elasticisers, viscosity-controlling agents, thickeners and adhesives, to obtain an antimicrobial barrier effect and as a medical device in wound treatment.

The following examples provide a detailed description of the invention.

EXAMPLE 1

Synthesis of Soluble Aggregates with a $[B]/[C_{CTL}]$ Molar Ratio of 0.002—(CTL Hydrochloride)

2.2 g of lactose monohydrate is introduced into a 250 ml 3-necked flask, and solubilised in 21 ml of water. 750 mg of chitosan is introduced, and 270 µl of glacial acetic acid is added. The system is then placed under heating in an oil bath at 60° C. with mechanical stirring until the polymer is completely solubilised. 370 mg of picoline borane complex (pic-BH$_3$) is dissolved in 3.0 ml of methanol and added to the chitosan and lactose solution. The reaction proceeds under stirring at 60° C. for 4 hours. At the end of the reaction, the crude reaction product is diluted with 27 ml of water. The bath is heated to 40° C., and a solution containing 400 mg of NaOH in 100 ml of methanol is dripped into it to precipitate the polymer. The solid is left to decant, the supernatant is removed, and 6 washes are performed with a 90% V/V solution of methanol/0.1N HCl, followed by a last wash in methanol only. The solid is dried at low pressure. 1.4 g of dry solid is recovered, and used to determine the residual boron content by complexing with azomethine-H and spectrophotometric analysis ("Boron Analysis from Dietary Supplements" by Anca-Michaela Bulearca et al., REV.CHIM. (Bucharest) 65, No. 1, 2014); said content amounts to 60 ppm. The degree of substitution of lactitol residue per repeating unit of chitosan (DS) is 0.53.

EXAMPLE 2

Synthesis of Soluble Aggregates with a $[B]/[C_{CTL}]$ Molar Ratio of 0.009—(CTL Hydrochloride)

2.2 g of lactose monohydrate is introduced into a 250 ml 3-necked flask, and solubilised in 21 ml of water. 750 mg of chitosan is introduced, and 270 µl of glacial acetic acid is added. The system is then placed under heating in an oil bath at 60° C. with mechanical stirring until the polymer is completely solubilised. 370 mg of picoline borane complex (pic-BH$_3$) is dissolved in 3.0 ml of methanol and added to the chitosan and lactose solution. The reaction proceeds under stirring at 60° C. for 4 hours. At the end of the reaction, the crude reaction product is diluted with 27 ml of water. The bath is heated to 40° C., and a solution containing 400 mg of NaOH in 100 ml of methanol is dripped into it to precipitate the polymer. The solid is left to decant, the supernatant is removed, and 6 washes are performed with a 95% V/V solution of methanol/0.4N HCl, followed by a last wash in methanol only. The solid is dried at low pressure. 1.3 g of dry solid with a DS of 0.50 is recovered and used to determine the residual boron content by complexing with azomethine-H and spectrophotometric analysis according to the method described in example 1; said content amounts to 240 ppm.

EXAMPLE 3

Synthesis of Soluble Aggregates with a $[B]/[C_{CTL}]$ Molar Ratio of 0.001—(CTL Hydrochloride)

2.2 g of lactose monohydrate is introduced into a 250 ml 3-necked flask, and solubilised in 21 ml of water. 750 mg of chitosan is then introduced, and 270 µl of glacial acetic acid is added. The system is then placed under heating in an oil bath at 60° C. with mechanical stirring until the polymer is completely solubilised. 400 mg of picoline borane complex (pic-BH$_3$) is dissolved in 3.0 ml of methanol and added to the chitosan and lactose solution. The reaction proceeds under stirring at 60° C. for 4 hours. At the end of the reaction, the crude reaction product is diluted with 27 ml of water. The bath is heated to 40° C., and 10 ml of water containing 0.6 ml of 12N HCl is added. The system is adjusted to room temperature, and acetone is dripped into it to induce the precipitation of the polymer. The solid is left to decant, the supernatant is removed, and 6 washes are performed with an 80% V/V solution of acetone/water, followed by a last wash in acetone only. The solid is dried at low pressure. 1.5 g of dry solid with a DS of 0.58 is recovered, and used to determine the residual boron content by complexing with azomethine-H and spectrophotometric analysis according to the method described in the previous examples; said content amounts to 30 ppm.

EXAMPLE 4

Synthesis of Soluble Aggregates with a $[B]/[C_{CTL}]$ Molar Ratio of 0.05—(CTL Acetate)

2.2 g of lactose monohydrate is introduced into a 250 ml 3-necked flask, and solubilised in 21 ml of water. 750 mg of chitosan is then introduced, and 270 µl of glacial acetic acid is added. The system is then placed under heating in an oil bath at 60° C. with mechanical stirring until the polymer is completely solubilised. 400 mg of picoline borane complex (pic-BH$_3$) is dissolved in 3.0 ml of methanol and added to the chitosan and lactose solution. The reaction proceeds under stirring at 60° C. for 4 hours. At the end of the reaction, the crude reaction product is diluted with 27 ml of water. The bath is heated to 40° C., and 4.2 ml of glacial acetic acid is added. The system is adjusted to room temperature, and acetone is dripped into it to induce the precipitation of the polymer. The solid is left to decant, the supernatant is removed, and 6 washes are performed with a 90% V/V solution of methanol/water, followed by a last wash in methanol only. The solid is dried at low pressure. 1.5 g of dry solid with a DS of 0.55 is recovered, and used to determine the residual boron content by complexing with azomethine-H and spectrophotometric analysis according to the method described in the previous examples; said content amounts to 1400 ppm.

EXAMPLE 5

Synthesis of Soluble Aggregates with a $[B]/[C_{CTL}]$ Molar Ratio of 0.007—(CTL Nitrate)

2.2 g of lactose monohydrate is introduced into a 250 ml 3-necked flask, and solubilised in 21 ml of water. 750 mg of chitosan is then introduced, and 270 µl of glacial acetic acid is added. The system is then placed under heating in an oil bath at 60° C. with mechanical stirring until the polymer is completely solubilised. 350 mg of picoline borane complex (pic-BH$_3$) is dissolved in 3.0 ml of methanol and added to the chitosan and lactose solution. The reaction proceeds under stirring at 60° C. for 4 hours. At the end of the reaction, the crude reaction product is diluted with 27 ml of water. The bath is heated to 40° C., and 10 ml of water containing 1.2 ml of 6N HNO$_3$ is added. The system is adjusted to room temperature, and acetone is dripped into it to induce the precipitation of the polymer. The solid is left to decant, the supernatant is removed, and 1 wash is conducted with an 80% V/V solution of methanol/water followed by 2 washes with a 90% V/V solution of methanol/water and a last wash in methanol only. The solid is dried at low pressure. 1.1 g of dry solid with a DS of 0.45 is recovered, and used to determine the residual boron content by complexing with azomethine-H and spectrophotometric analysis according to the method described in the previous examples; said content amounts to 180 ppm.

COMPARATIVE EXAMPLE 6

A chitosan conjugated with lactose was prepared by the procedures reported in EP 2310448, EP 2029629, WO 2010/010122 and WO 2007/135116.

1.5 g of commercial chitosan is solubilised with 110 ml of a solution obtained by mixing 55 ml of an aqueous solution of 1% w/V acetic acid at pH=4.5 with 55 ml of methanol. 60 ml of a solution pre-prepared with 2.2 g of lactose, 0.90 g of NaCNBH$_3$, 30 ml of methanol and 30 ml of a 1% w/V aqueous solution of acetic acid at pH=4.5 is added to said solution. The crude reaction product is maintained under magnetic stirring for 24 hours at room temperature and then transferred to a dialysis bag with a 12 kDa cut-off and dialysed at 4° C. Two changes of external solution are performed, first with a solution of 0.1M NaCl and then with deionised water only, until a residual conductivity of 4 µS is reached. The polymer solution is filtered through a filter with a porosity of 0.45 µm and then freeze-dried. The boron residue is determined on the freeze-dried product, and amounts to 28 ppm, which corresponds to a boric acid/chitosan-lactose molar ratio<0.001. This sample was used for rheological characterisation by comparison with the CTL according to the invention (FIG. 2).

COMPARATIVE EXAMPLE 7

For comparative purposes, the preparation of glycated chitosans was replicated according to the synthesis procedure described in U.S. Pat. No. 5,747,475 (column 9, lines 30-59 and column 10, lines 1-57), using lactose as model oligosaccharide. As U.S. Pat. No. 5,747,475 does not specify the pH conditions used, the proof of synthesis was repeated at three different pH values (2.5, 5.5 and 7), obtained by using chitosan hydrochloride, chitosan acetate and commercial chitosan alone respectively; in the latter case, the polymer granules swell, but do not solubilise during the reaction. By applying the process described in U.S. Pat. No. 5,747,475 to chitosan-lactose, a DS<5% is obtained in the products of the two reactions in homogeneous (acid) phase, and no structural modification is observed when the reaction is conducted in heterogeneous phase at a neutral pH. The samples obtained proved to be insoluble in water at a neutral pH, and therefore unsuitable for the applications according to the invention.

The invention claimed is:

1. Pharmaceutical or cosmetic compositions or medical devices comprising adducts of boric acid and chitosan wherein the amino groups of the D-glucosamine units are linked to residues of polyol or alditol oligosaccharides, the molar ratio between boric acid and the repeating unit of chitosan ranging from 0.001 to 4, said adducts being in a mixture with compatible carriers or excipients and optionally with other active ingredients.

2. Adducts according to claim 1 wherein the oligosaccharides are selected from glucose, galactose, lactose, cellobiose, cellotriose, maltose, maltotriose, maltotetraose, chitobiose, chitotriose, melibiose, agarobiose and carrabiose.

3. Adducts according to claim 2 wherein the oligosaccharide is lactose.

4. Adducts according to claim 1, wherein at least 30% of the amino groups of the D-glucosamine units are bonded to oligosaccharide residues.

5. Adducts according to claim 1 wherein the chitosan has a molecular weight ranging from 300 kDa to 1500 kDa.

6. Adducts according to claim 1 having a polymer concentration viscosity scaling law ($\eta \propto C^\alpha$) wherein the value of a ranges from 4.5 to 6.2.

7. Adducts according to claim 1 in the form of salts with acids.

8. Process for the preparation of the adducts of claim 1, said method comprising:

a) adding boric acid, derivatives or precursors thereof, and oligosaccharide to a chitosan aqueous solution at a polymer concentration greater than or equal to 1.5%; and b) purifying the soluble adducts obtained in step a) by precipitating with non-solvents selected from methanol, ethanol, isopropanol, n-propanol, acetone or mixtures thereof and washing with acid solutions of hydrochloric acid, nitric acid, sulphuric acid, phosphoric acid, acetic acid, trichloroacetic acid, trifluoroacetic acid, formic acid or mixtures thereof.

9. Process according to claim 8 wherein the boric acid derivatives or precursors thereof are selected from sodium borohydride, sodium cyanoborohydride, sodium acetate borohydride, sodium triacetoxyborohydride, lithium borohydride, potassium borohydride, tetrabutylammonium borohydride, calcium borohydride, magnesium borohydride, tetraethylammonium borohydride, methyltrioctylammonium borohydride, bis(triphenylphosphine) copper (I) borohydride, borax, potassium tri(1-pyrazolyl) borohydride, cetyltrimethylammonium borohydride, tetrahydrofuran-borane complex, picoline-borane complex, dimethylsulphide-borane complex, pyridine-borane complex, trimethylamine-borane complex, triethylamine-borane complex, morpholine-borane complex, t-butylamine-borane complex, ammonia-borane complex, diphenylphosphine-borane complex, 4-methylmorpholine borane complex and ethylenediamine-borane complex.

\* \* \* \* \*